United States Patent [19]

Mazurek

[11] Patent Number: 4,665,261
[45] Date of Patent: May 12, 1987

[54] HYDROCARBON CONVERSION PROCESS USING A MOLTEN SALT

[75] Inventor: Harry Mazurek, Bala Cynwyd, Pa.

[73] Assignee: Atlantic Richfield Company, Los Angeles, Calif.

[21] Appl. No.: 747,548

[22] Filed: Jun. 21, 1985

[51] Int. Cl.$^4$ .............................................. C07C 2/00
[52] U.S. Cl. .................................. 585/500; 585/415; 585/417; 585/418; 585/654; 585/656; 585/658; 585/661; 585/700; 585/943
[58] Field of Search ............... 585/500, 943, 654, 656, 585/658, 661, 541, 700, 415, 417, 418; 423/DIG. 12

[56] References Cited

U.S. PATENT DOCUMENTS

| | | | |
|---|---|---|---|
| 3,081,256 | 3/1963 | Hendal et al. | 585/650 |
| 4,443,644 | 4/1984 | Jones et al. | 585/500 |
| 4,443,645 | 4/1984 | Jones et al. | 585/500 |
| 4,443,647 | 4/1984 | Jones et al. | 585/500 |
| 4,443,648 | 4/1984 | Jones et al. | 585/500 |
| 4,443,649 | 4/1984 | Jones et al. | 585/500 |
| 4,444,984 | 4/1984 | Jones et al. | 585/500 |
| 4,499,322 | 2/1985 | Jones et al. | 585/500 |
| 4,517,398 | 5/1985 | Sofranko | 585/500 |
| 4,523,049 | 6/1985 | Jones et al. | 585/500 |
| 4,544,787 | 10/1985 | Breder, Jr. | 585/500 |

*Primary Examiner*—William R. Dixon, Jr.
*Assistant Examiner*—Cynthia A. Prezlock
*Attorney, Agent, or Firm*—Coleman R. Reap

[57] ABSTRACT

A process for converting low molecular weight gases such as methane and natural gas to higher hydrocarbons by means of a molten salt containing a synthesizing contact agent. The gas is contacted with a molten salt containing a metal, the oxide of which is reduced when contacted with methane at a temperature in the range of 500° to 1000° C. to produce higher hydrocarbons and water. The reduced metal oxide/salt mixture may be regenerated to the active state by contacting the molten salt mixture with an oxygen-containing gas.

13 Claims, 1 Drawing Figure

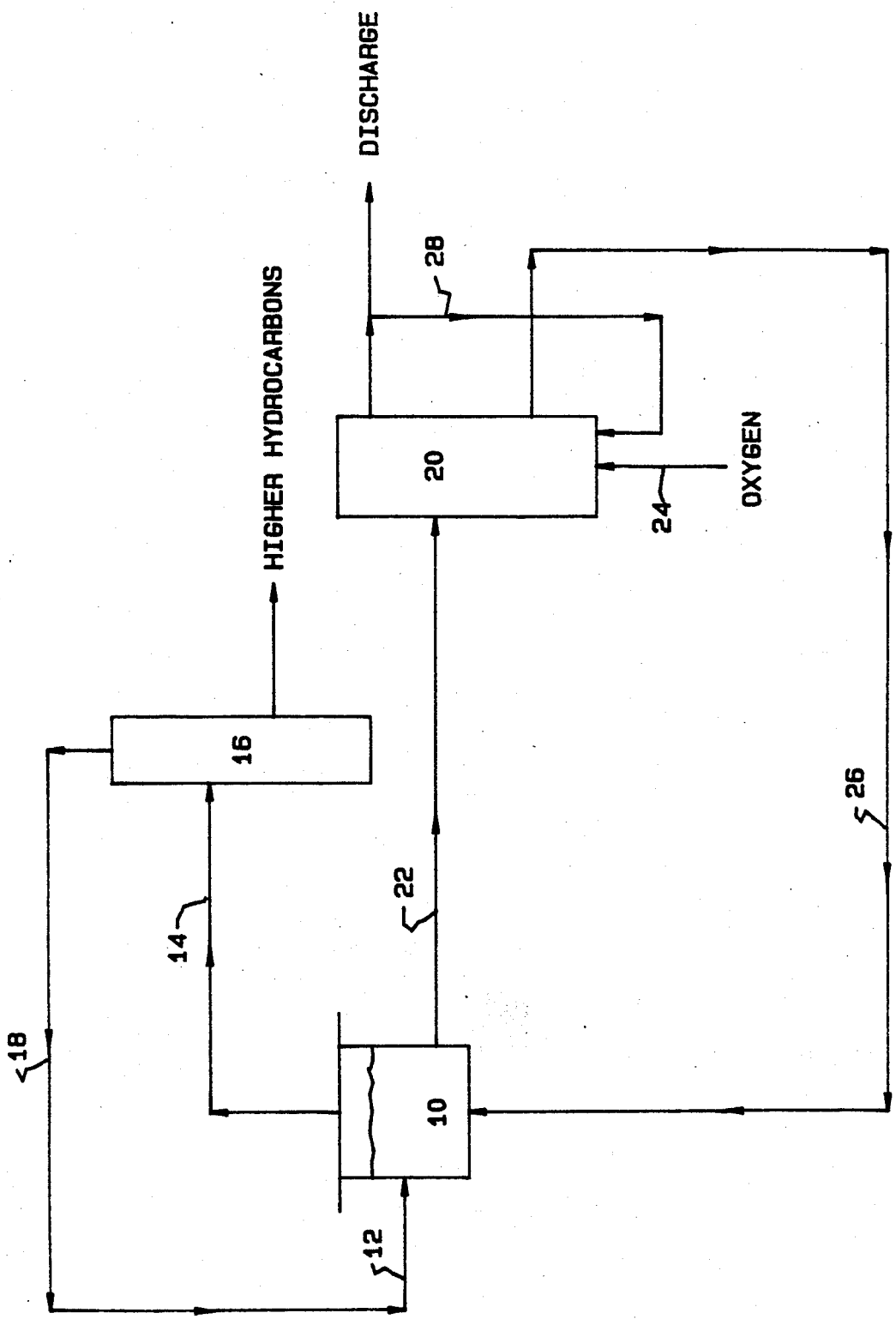

HYDROCARBON CONVERSION PROCESS USING A MOLTEN SALT

BACKGROUND OF THE INVENTION

1. Field of the Invention

This invention relates to the synthesis of hydrocarbons from a methane source. A particular application of this invention is a method for converting natural gas to more readily transportable material using a methane conversion catalyst formed using a reducible metal oxide and a molten salt.

2. Description of the Pertinent Art

A major source of methane is natural gas. Other sources of methane have been considered for fuel supply (e.g., the methane present in coal deposits or formed during mining operations). Relatively small amounts of methane are also produced in various petroleum processes.

The composition of natural gas at the wellhead varies, but the major hydrocarbon present is methane. For example, the methane content of natural gas may vary within the range of about 40 to about 95 volume percent. Other constituents of natural gas include ethane, propane, butane, pentane (and heavier hydrocarbons), hydrogen sulfide, carbon dioxide, helium, and nitrogen.

Natural gas is classified as dry or wet, depending upon the amount of condensable hydrocarbons contained in it. Condensable hydrocarbons generally comprise $C_3+$ hydrocarbons, although some ethane may be included. Gas conditioning is required to alter the composition of wellhead gas; processing facilities usually being located in or near the production fields. Conventional processing of wellhead natural gas yields processed natural gas containing at least a major amount of methane.

Large-scale use of natural gas often requires a sophisticated and extensive pipeline system. Liquefaction has also been employed as a transportation means, but processes for liquefying, transporting and revaporizing natural gas are complex, energy intensive and require extensive safety precautions. Transport of natural gas has been a continuing problem in the exploitation of natural gas resources. It would be extremely valuable to be able to convert methane (e.g., natural gas) to more readily transportable products. Moreover, direct conversion to olefins such as ethylene or propylene would be extremely valuable to the chemical industry.

Recently, it has been discovered that methane may be converted to higher hydrocarbons by a process which comprises contacting methane with an oxidative synthesizing agent at synthesizing conditions (e.g., at a temperature selected within the range of about 500° to about 1000° C.). An oxidative synthesizing agent is a composition having as a principal component at least one oxide of at least one metal, which composition produces higher $C_2+$ hydrocarbon products, water and a composition comprising a reduced metal oxide when contacted with methane at synthesizing conditions. Reducible oxides of several metals have been identified which are capable of converting methane to higher hydrocarbons. In particular, oxides of manganese, tin, indium, germanium, lead, antimony, praseodymium, and bismuth are most useful.

Typically, the oxidative synthesizing agent is in fluidized bed reactors and in packed bed cycling operations.

In the fluidized bed converters, separated fluidized bed vessels are used for reaction and regeneration; the agent particles are fluidized by the methane feed gas in a reactor and by the oxidizing gas (e.g., air) in a regenerator, with the agent transferring continuously between the two vessels. This process has the advantages of steady-state operation and good temperature control, facilitating well controlled product compositions and per pass conversions. However, the motion in the fluidized bed causes the agent particles to break up into fines by attrition; the fines then elute out of the vessels with the effluent gases, thereby reducing the service life of the agents. The fluidized particles are also abrasive, and tend to erode the internals of the vessels and piping. Extra flue gas treatment steps may also be needed to control emission of entrained particulates.

In the packed bed converters, the agent is packed into a single vessel where it is sequentially and cyclically reduced (reaction with the methane feed), regenerated (oxidized with air or oxygen), and cooled with gas to remove the heat released during regeneration from the agent particles. Cycle times of less than 5–10 minutes are typical. The cyclic packed bed converter is inherently nonsteady state, with both agent temperatures and bound oxygen concentrations varying with both time and position in the bed. Consequently, during the reductive reaction step, the product distribution, local bed temperature, and conversion of the feed varies over time. Thus, this type of converter is difficult to control and is subject to severe mechanical stress due to rapid thermal cycling.

In an article entitled "Partial Oxidation of O-xylene in Melts containing Vanadium Pentoxide" by Satterfield and Loftus, the authors disclose contacting methods for catalyzed gas-phase reactions to include bubbling reactants through a melt which acts as an oxidizing agent or as a catalyst. The reactants would be oxidized by the melt in one reactor, and the reduced melt reoxidized by a second gas stream such as air in a second reactor, and then recirculated to the first reactor.

In U.S. Pat. No. 4,107,280, there is disclosed a process for oxidizing hydrogen halide by means of a catalytically active molten salt. The molten salt is comprised chiefly of alkali metal pyrosulfates and sulfates, and a lesser amount of vanadium pentoxide which serves as a source of oxygen for reaction with the hydrogen halide. The gaseous effluent stream includes halogen, steam, and unreacted hydrogen halide, but no free oxygen. The molten salt is transported to a second reactor where it is contacted with an oxygen-bearing gas such as air. Other soluble metal oxides may be used for the oxidation of hydrogen chloride, including copper, iron, chromium or manganese. Less suitable metal oxides include lead, nickel, cobalt or uranium.

Accordingly, an object of this invention is to provide an improved process for converting methane to higher hydrocarbons. A further object of this invention is an improved method of contacting the methane with an oxidative synthesizing agent while effectively transferring heat to the methane feed and providing a uniform thermal atmosphere.

Other aspects, objects and the several advantages of this invention will become apparent to those skilled in the art upon reading this Specification and the appended claims.

SUMMARY OF THE INVENTION

An improved hydrocarbon conversion process has been discovered which comprises contacting hydrocarbons, preferably a gas comprising methane, with a contact agent associated with a molten salt bath at conditions to convert the hydrocarbons; the agent comprising at least one metal, the oxide of which is reduced, and which produces higher hydrocarbon products and water when contacted with methane at a temperature selected within the range of about 500° to about 1000° C.; and the molten salt bath having a melting point below the selected temperature.

DETAILED DESCRIPTION OF THE INVENTION

Referring to FIG. 1, the general process of this invention for converting a low molecular weight gas to higher hydrocarbons is shown. A gas such as natural gas or methane is fed to a molten salt reaction zone 10 via a line 12. The reaction zone 10 contains a molten salt mixture in which active metal oxide is dissolved or slurried. When contacted with the molten salt mixture, the methane gas is converted by reaction with the contact agent to higher hydrocarbons.

The effluent gas mixture leaving the reaction zone 10 via a line 14 contains a mixture of steam, unreacted methane gas, higher hydrocarbons (including ethylene, ethane, propane, and butane), carbon oxides, and coke. It is an advantage that little or no oxygen gas is formed in the reaction zone 10 to limit the formation of combustion products of the hydrocarbon reactants and products. The higher hydrocarbons and the excess methane can be separated by a conventional gas separation apparatus 16. The recovered methane may be recycled to the reaction zone 10 via a line 18 to line 12.

Contact with the methane gas causes the contact agent in the molten salt mixture to be reduced to a lower valence state. The exact nature of the reduced metal oxide is unknown, and so is referred to herein as "reduced metal oxide". As the content of the molten salt mixture is reduced, it becomes less active and effective. When the activity has reached a predetermined level, the contact agent is regenerated. This regeneration is accomplished by transporting the spent molten salt mixture to a molten salt regeneration zone 20 via a line 22. The molten salt mixture is then contacted with a stream of oxygen-bearing gas such as air introduced via a line 24. The contact agent reacts with the oxygen in the gas and, thus, is regenerated to its higher valence state. The regenerated molten salt mixture is returned to the reaction zone 10 via a line 26. The effluent gas from the regeneration zone 20 either is recirculated back to the regeneration zone 20 via a line 28 to line 24 or discharged from the system.

The heat generated by the oxidation of the contact agent may be removed by cooling coils within the regeneration zone 20, by external heat exchangers in line 26 returning the molten salt mixture to the reaction zone 10 or in line 22 transporting the molten salt mixture to the regeneration zone 20, or by condensing the vapors of the molten salt mixture boiling in the regeneration zone 20. During regeneration, the temperature of the molten salt mixture and, consequently, the contact agent should not exceed 1200° C. or lower, depending on the metal included in the contact agent.

It is important to minimize contact of the methane-containing gas with the oxygen-containing gas to eliminate the possibility of explosion or fire. The regeneration zone effluent gas or the steam effluent from the reaction zone may be used to purge the molten salt mixture before entrance to the regeneration zone and following exit from the regeneration zone of any entrained oxygen gas.

In a preferred embodiment not shown in the Figure, the molten salt mixture may be fed from the reaction zone 10 to an interim zone before the regeneration zone 20. To this interim zone, the effluent gas from the regeneration zone 20 may be used to purge the molten salt mixture of any entrained methane gas. The regeneration zone off-gas should be relatively free of oxygen and may be cooled prior to contact with the molten salt mixture such that the temperature of the molten salt mixture is reduced to just above the melting point. The cooled molten salt mixture is then fed to the regeneration zone 20 where the temperature is increased to the operating temperature of the reaction zone 10. If necessary and not detrimental to the molten salt mixture, the temperature within the regeneration zone 20 may be allowed to exceed the operating temperature. Prior to recycling the molten salt mixture to the reaction zone 10, however, the molten salt mixture may be cooled to operating temperature by conventional heat exchange equipment.

Although the methane conversion process produces substantial quantities of water, almost all of the water produced exits the reaction zone as steam. During the regeneration process, it may be desirable to remove any water which does not exit the process.

The steps are preferably repeated at least periodically, and more preferably the steps are continuous.

Alternatively, the process may be carried out in a single reactor apparatus containing molten salt and contact agent with intermittent or pulsed flow of a methane feed gas followed by intermittent or pulsed flow of a second gas comprising oxygen (e.g., oxygen, oxygen diluted with an inert gas, or air, preferably air). Again, purge methods should be employed between the pulsed flows to insure that the prior gas has been stripped from the molten salt.

The contact agent of this invention is a composition comprising at least one reducible oxide of at least one metal. The reducible oxide produces higher hydrocarbon products, water and a reduced metal oxide when contacted with methane at a temperature selected within the range of about 500° to about 1000° C. The term "reducible" is used to identify those oxides of metals which are reduced by contacting methane at synthesizing conditions. The term "oxide(s) of metal(s)" includes: (1) one or more metal oxides (i.e., compounds described by the general formula $M_xO_y$ wherein M is a metal, O is oxygen, and the subscripts x and y designate the relative atomic proportions of metal and oxide in the composition); and/or (2) one or more oxygen-containing metal compounds; provided that such oxides and compounds have the capability of performing to produce higher hydrocarbon products as set forth herein.

The preferred contact agents comprise reducible oxides of metals selected from a group consisting of manganese, tin, indium, germanium, antimony, lead, bismuth, and mixtures thereof. The particularly preferred contact agents comprise reducible oxides of manganese and mixtures of reducible oxides of manganese with other oxidative synthesizing agents.

In the preferred embodiment, in addition to manganese, other reducible oxides of metals may be included in the compositions of this invention. These other reducible oxides of metals include tin, indium, germanium, antimony, lead, bismuth, praseodymium, terbium, cerium, iron, and ruthenium.

One class of preferred compositions is characterized by the substantial absence of catalytically effective amounts of nickel and the noble metals (e.g., rhodium, palladium, silver, osmium, iridium, platinum, and gold) and compounds thereof to minimize the deleterious catalytic effects of such metals and compounds thereof. For example, at the conditions (e.g., temperature) under which the present compositions are used, these metals tend to promote coke formation and oxides of these metals tend to promote the formation of combustion products ($CO_x$), rather than the desired hydrocarbons. The term "catalytically effective" is used to identify that quantity of nickel, the noble metals, and compounds thereof which, when present, substantially changes the distribution of products obtained when employing the compositions of this invention.

The contact agent particles should be finely divided, with large specific surface areas, to facilitate suspension in the molten salt mixture and to minimize mass transfer resistance within the catalyst particles.

Preferably, the contact agent is associated with a support comprising oxides of silicon, oxides of alkaline earth metals, and mixtures thereof. Preferably, the support comprises at least two oxides. Preferably, at least one of the oxides is an alkaline earth oxide and the second oxide is selected from a group comprising silica, alumina, and mixtures thereof. More preferably, the first oxide comprises magnesia and the second oxide comprises silica.

The preferred mole ratio of the first oxide to the second oxide is 1:1 or greater, and more preferably is in the range of about 30:1 to about 5:1. Particularly good results are obtained when this ratio is about 5:1.

Preferably, the metal oxide comprises an alkali metal. More preferably, the metal oxide comprises an alkali metal selected from a group consisting of lithium, sodium, potassium, rubidium, cesium, and mixtures thereof.

The composition may be prepared from silica and alkaline earth oxides such as MgO, CaO, SrO, and BaO. However, other sources of mixed oxides may also be employed (e.g., $MgSiO_4$, $MgSiO_3$, $Mg_2SiO_4$, $CaMg(SiO_3)_2$, and $Ca_2BaSi_3O_9$).

Preferably, a hydroxylated magnesia is utilized in the support. The term "hydroxylated magnesia" means a magnesia derived from magnesium hydroxide or a magnesium-containing component contacted with a hydroxyl-containing component. The hydroxylated magnesia is preferably derived from magnesium hydroxide (e.g., magnesia produced from sea water). One such suitable magnesia is commercially available from CRI Industries as MgO-700.

Alternatively, the hydroxylated magnesia may be derived from sources other than magnesium hydroxide such as a magnesium-containing component contacted with a hydroxyl-containing material (e.g., one or more compounds including hydroxyl groups). Such hydroxyl-containing material includes sodium hydroxide, potassium hydroxide, lithium hydroxide, slake lime, calcium hydroxide, and hydroxides of barium. One method of producing the present hydroxylated magnesia comprises contacting a magnesium-containing component with (a) water for an extended period or (b) boiling water. Any suitable magnesium-containing component may be employed to produce hydroxylated magnesia. Examples include magnesia, magnesium chloride, and magnesium salts.

Preferably, the support is precalcined prior to the addition of the at least one metal. The support is calcined at an elevated temperature in an oxygen-containing gas. The particular precalcining temperature will vary, but preferably it will be between about 300° and about 1200° C.

The support is preferably prepared in powdered form, more preferably having a particle size ranging from about 20 to about 200 microns, and still more preferably about 100 microns. The support is dried to the extent that upon subsequent sintering the particles do not steam or explode. Preferably, the particles have a water content of less than about 1.0 weight percent.

Preferably, the support is sintered to an elevated temperature (i.e., heated to a high temperature without melting the support) by exposure for a short time to a temperature high enough to cause at least partial fusion of the surface of the particles. This exposure can occur before or after the addition of the metal which forms at least one reducible oxide (e.g., derived from sodium or lithium permanganate, or mixtures of manganese and sodium, or lithium salts). The elevated (sintering) temperature varies with the composition of the material being sintered. In one preferred embodiment, the elevated temperature is equal to about 0.33 of the normal melting temperature of the material of the support.

Exposure to the high temperature may be accomplished by allowing the particles to briefly contact a flame or a hot surface. Alternatively, a laser or other electromagnetic radiation source with a limited depth of surface penetration of the support may be used. The degree of surface sintering can be controlled by the temperature of the flame or hot surface, by the intensity of the light, or by the length of time of exposure.

The particles should be removed from the heat source quickly so that the effect of the sintering is confined to the depth desired. Removal from the flame or hot surface can be accomplished by several means—by transporting the particles out of the region of the hot substance, by cooling the hot substance with another material, by contacting the particles with a heat sink to remove the heat absorbed from the hot substance, or by combinations of these and other methods. When a laser is used, its light can be diverted or adsorbed. Removal of heat by radiation or conduction is preferred.

The addition of steam or an inert gas (such as nitrogen) or a reactive gas (such as hydrogen chloride) is preferred to control the sintering process.

Preferred sintering temperatures for the support material are in the range of about 1690° to about 5070° F. for magnesia and about 1040° to about 3110° F. for silica. Sintering of the support may take place in a period of time in the range of about 0.5 minute to about 15 minutes or more, preferably in a period of time in the range of about 1 minute to about 10 minutes.

Preferably, the support compositions exhibit a surface area ranging from about 30 to about 90 square meters per gram.

Preferably, the contact agent composition of this invention comprises manganese, the oxide of which is reducible, at least one alkali metal or compound thereof, and a support comprising at least one member of a group consisting of oxides of silicon, oxides of alkaline earth metals, and mixed oxides of silicon and at least one alkaline earth metal. In general, the preferred compositions contain more than about 50 weight percent of the support, more preferably they contain more than about 60 weight percent of the support. Stated in another way, manganese is preferably present in an amount within the range of about 1 to about 40 weight percent based on the combined weight of the manganese and the support, more preferably within the range of about 5 to about 30 weight percent. When the composition is prepared from alkaline earth metal oxides, this manganese loading is more preferably within the range of about 10 to about 20 weight percent. The atomic ratio of alkali metal to manganese is preferably within the range of about 0.01:1 to about 10:1.

Examples of specific embodiments within this broad class are described below.

$MnA_aSi_bO_x$

Another class of compositions within the scope of this invention comprises manganese-containing oxides, at least one alkali metal or compound thereof, and at least one oxide of silicon, said composition satisfying the formula:

$$MnA_aSi_bO_x$$

wherein:
A is at least one alkali metal,
a is within the range of about 0.01 to about 10,
b is within the range of about 0.5 to about 90, and
x is the number of oxygen atoms required by the valence states of the other elements, Preferably, b is within the range of about 0.9 to about 17.4, more preferably within the range of about 2 to about 15. The silicon component may be provided as silica. However, use of other materials is also within the scope of this invention. For example, the defined composition may be derived from braunite, a native manganese silicate having the formula $MnSiO_3 \cdot Mn_2O_3$.

$MnA_aMg_bO_x$

Another class of compositions within the scope of this invention comprises manganese-containing oxides, at least one alkali metal, and at least one oxide of magnesium, said composition satisfying the formula:

$$MnA_aMg_bO_x$$

wherein:
A is at least one alkali metal,
a is within the range of about 0.01 to about 10,
b is within the range of about 1.4 to about 130, and
x is the number of oxygen atoms required by the valence states of the other elements.

Preferably, b is within the range of about 3 to about 80, more preferably within the range of about 5 to about 12. The magnesium component is preferably provided as magnesia.

$MnA_aB_bO_x$

Another class of compositions within the scope of this invention comprises manganese-containing oxides, at least one alkali metal or compound thereof, and at least one member of a group consisting of oxides of calcium, strontium, and barium, said composition satisfying the formula:

$$MnA_aB_bO_x$$

wherein:
A is at least one alkali metal,
B is at least one member of the group consisting of calcium, strontium, and barium,
a is within the range of about 0.01 to about 10,
b is within the range of about 0.1 to about 100, and
x is the number of oxygen atoms required by the valence states of the other elements.

Preferably, b is within the range of about 1 to about 7.

Compositions described by the formula $MnA_aCa_bO_x$ are presently preferred. In this case, b is preferably within the range of about 0.4 to about 100, more preferably within the range of about 4 to about 20.

Oxides of calcium, strontium, and barium are preferably provided as CaO, SrO, and BaO, respectively.

$MnA_aB_bSi_cO_x$

Another class of compositions within the scope of this invention comprises manganese-containing oxides, at least one alkali metal or compound thereof, and mixed oxides of silicon and alkaline earth metals, said composition satisfying the formula:

$$MnA_aB_bSi_cO_x$$

wherein:
A is at least one alkali metal,
B is at least one alkaline earth metal,
a is within the range of about 0.1 to about 10,
b is within the range of about 0.1 to about 90,
c is within the range of about 1 to about 90,
the sum of b plus c is greater than about 1, and
x is the number of oxygen atoms required to satisfy the valence states of the other elements.

When B is magnesium, b is preferably within the range of about 0.6 to about 10. When B is calcium, b is preferably within the range of about 0.4 to about 10. When B is barium, b is preferably within the range of about 0.1 to about 5.

While the relative amounts of alkaline earth metal and silicon in the compositions are not believed to be narrowly critical, preferred silica magnesia components have been identified. One component consists of silica-magnesia wherein the ratio c:b is within the range of about 2:1 to about 3:1. Another component consists of magnesia-silica wherein the ratio b:c is within the range of about 5:1 to about 30:1.

Other additives may also be incorporated into the compositions of this invention. For example, the addition of a phosphorus component has been found to enhance the stability of the compositions. When used, phosphorus may be present up to an amount providing a phosphorus-to-manganese ratio of about 2:1. If phosphorus is employed, it is desirable to provide it during catalyst preparation in the form of phosphates of alkali metals (e.g., orthophosphates, metaphosphates, and pyrophosphates). Pyrophosphates are preferred. Sodium pyrophosphate is particularly preferred. Phosphorus can be provided in other forms though. Examples include orthophosphoric acid, ammonium phosphates, and ammonium hydrogenphosphates.

Further examples of other components which may be present in the compositions of this invention include halogen and chalcogen components. Such components may be added either during preparation of the catalyst or during use.

The preferred contact agent of this invention contains, in addition to the foregoing elements, at least one alkali metal. Sodium and/or compounds thereof are a particularly preferred alkali metal component. Except as noted elsewhere herein, the atomic ratio in which these materials are combined to form the contact agent is not narrowly critical. However, the preferred atomic ratio of the reducible oxide component (expressed as the metal, e.g., Mn) to the alkali metal component (expressed as the metal, e.g., Na) is within the range of about 0.1:1 to about 100:1, more preferably within the range of about 0.3:1 to about 10:1. The preferred mole ratio of silica or alumina to alkali metal is about 50:1 to about 1:1, more preferably about 0.5:1 to about 10:1. Most preferably, the ratio is about 1:1 to about 3:1.

The alkali metal component may be added to the support before or during precipitation, coprecipitation, or impregnation of the reducible oxide and the support.

The support or agent may be contacted with a suitable alkali metal component which should not interfere with the support function, the reducible oxide function, or the process for combining the support with the reducible oxide. Preferably, the alkali metal component is a basic composition of the alkali metal. More preferably, the alkali metal component is selected from a group consisting of sodium hydroxide, sodium acetate, lithium hydroxide, lithium acetate, and mixtures thereof.

The contact agent can be prepared by any suitable method. Conventional methods such as precipitation, coprecipitation, impregnation, granulation, and spray drying can be used.

Suitable methods of preparation of the contact agent include mixing an aqueous slurry of magnesia and silica gel with a solution of reducible oxides, and preparation and drying a support followed by impregnation with the suitable metal compounds which include acetates, acetylacetonates, oxides, carbides, carbonates, hydroxides, formates, oxalates, nitrates, phosphates, sulfates, sulfides, tartrates, fluorides, chlorides, bromides or iodides of the metals.

After the mixing of the slurry with the solution or after the impregnation, the resulting composite is dried in an oven to remove solvent and the dried solid is prepared for use by calcining at elevated temperatures in an oxygen-containing gas (e.g., air) prior to use in the process of this invention. Particular calcination temperatures will vary, depending upon the particular metal compound or compounds employed. Preferably, the air temperature is selected within the range of about 300° to about 1200° C.

The molten salt should have a melting point below the lowest operating temperature of the system. The other ions present in the salt should have either a beneficial effect on the reaction yields or no effect at all. The viscosity of the molten salt at the operating temperature should be low to minimize the mass transfer resistance of the gases to the contact agent particles.

The molten salt selected should be inert with the contact agent to be slurried. With the agent to be dissolved in the salt, the salt may react as long as the mixture remains liquid and the contact agent remains effective.

Selection of salt should avoid problems such as surface tension effects and creeping of the molten salt up the walls of the reactor. Additionally, corrosiveness of the molten salt should be considered and balanced against its advantages. Inert, smooth and passivated reactor surfaces may be desirable to lessen such problems. Physical strength and resistance to thermal shock should be considered in selection of the reactor material.

In the molten salt mixture, it may be desirable that a gas disperser be added. Alternatively, or in addition to the gas disperser, the molten salt mixture may be formed to comprise inert particles which have very low surface areas, or high temperature surfactants or viscosity modifiers. The reaction zone may also be fitted with mechanical means to disperse the methane feed gas.

The exact nature of the contact agent and molten salt is not entirely known. The contact agent may be the reducible metal oxide alone or supported and may be (a) in the molten state; (b) dissolved and soluble with the molten salt; or (c) slurried as a dispersed distinct particle. The inerts added to the molten salt mixture may also melt, remain distinct particles or associate with the contact agent.

A salt composition suitable for use according to the present invention includes alkali metal halides, phosphates, borates, carbonates, sulfates, tungsten oxides, silicates, molybdenum oxides, alkaline earth metal halides, and mixtures thereof. Preferred salts are included in Table 1.

TABLE 1

| Salt | M.P. (°C.) | Mole % |
|---|---|---|
| CaF | 682 | 100 |
| BiF$_3$ | 727 | 100 |
| Na$_2$CO$_3$ | 854 | 100 |
| Li$_2$CO$_3$ | 735 | 100 |
| Bi$_2$(MoO$_4$)$_3$ | 643 | 100 |
| Li$_2$WO$_4$ | 742 | 100 |
| Na$_2$WO$_4$ | 696 | 100 |
| Na$_2$Si$_2$O$_5$ | 874 | 100 |
| Li$_2$B$_2$O$_4$ | 760 | 100 |
| Li$_2$B$_6$O$_{10}$ | 750 | 100 |
| Li$_2$B$_8$O$_{13}$ | 730 | 100 |
| Li$_2$B$_{10}$O$_{16}$ | 680 | 100 |
| Na$_2$B$_4$O$_7$ | 742 | 100 |
| Na$_2$B$_8$O$_{13}$ | 816 | 100 |
| Na$_2$B$_2$O$_5$ | 625 | 100 |
| Li$_2$BO$_2$ | 845 | 100 |
| Na$_2$SO$_4$ | 889 | 100 |
| Li$_2$WO$_4$/Na$_2$WO$_4$ | 490 | 45/55 |
| Na$_2$CO$_3$/K$_2$CO$_3$ | 710 | 56/44 |
| Li$_2$SO$_4$ | 859 | 100 |
| Li$_2$CO$_3$/Na$_2$CO$_3$/K$_2$CO$_3$ | 397 | 43.5/31.5/25.0 |
| KCl | 772 | 100 |
| LiCl | 610 | 100 |
| NaCl | 808 | 100 |
| MgCl$_2$ | 714 | 100 |

Of these, particularly suitable salts include lithium phosphate, sodium borate, lithium borate, and a mixture of lithium carbonate, sodium carbonate, and potassium carbonate eutectic at the selected operating temperature.

It is desirable to have the agent and support added to the molten salt mixture such that the agent and support are slurried as a distinct entity.

In the case of the addition of a feed gas dispersant, there are many suitable embodiments. One preferred embodiment includes the addition of a component which is stable at melt temperatures and relatively inert. Such components should have low activity with respect to the methane feed gas.

In the molten salt mixture, it is preferred that the contact agent and the support comprise from about 1 to about 75 volume percent of the mixture, more preferably from about 10 to about 50 volume percent. In the homogeneous salt mixture, the weight percent of contact agent should range from about 1 to about 75 percent, more preferably from about 20 to about 60 weight percent.

In addition to methane, the preferred feedstock employed in the method of this invention may contain other hydrocarbon or non-hydrocarbon components, although the methane content should typically be within the range of about 40 to about 100 volume percent, preferably about 80 to about 100 volume percent, more preferably about 90 to about 100 volume percent.

Operating temperatures for contacting the methane with the contact agent are preferably selected within the range of about 500° to about 1000° C.; the particular temperature selected depending upon the particular reducible metal oxide(s) employed in the contact agent. For example, reducible oxides of certain metals may require operating temperatures below the upper part of the recited range to minimize sublimation or volatilization of the metals (or compounds thereof) during methane contact. Examples include reducible oxides of indium, germanium and bismuth (operating temperatures will preferably not exceed about 850° C.).

Operating pressures for the methane contacting step are not critical to the presently claimed invention. However, both general system pressure and partial pressure of methane have been found to affect overall results. Preferred operating pressures are within the range of about 1 to about 30 atmospheres. The partial pressure of methane in the reaction zone is preferably maintained within the range of about 1 atmosphere to about 2 atmospheres.

Particles comprising reduced metal oxides in the molten salt are contacted with oxygen in an oxygen contact zone for a time sufficient to oxidize at least a portion of the reduced metal oxides to produce a reducible metal oxide and to remove (i.e., combust) at least a portion of any carbonaceous deposit which may form on the particles in the methane contact zone. The conditions of the oxygen contact zone will preferably include pressures of up to about 30 atmospheres, and average particle contact time within the range of about 1 minute to about 120 minutes. Sufficient oxygen is preferably provided to oxidize all reduced metal oxide to produce a reducible metal oxide and to completely combust any carbonaceous deposit material deposited on the particles.

Another more specific application for the compositions of this invention is the dehydrogenation of dehydrogenatable hydrocarbons. The process comprises contacting a gas comprising a dehydrogenatable hydrocarbon with a contact agent and molten salt of this invention to produce dehydrogenated hydrocarbon products, water, and a composition comprising a reduced metal oxide. Dehydrogenatable hydrocarbons include a wide variety of hydrocarbons (e.g., $C_2+$ alkanes, cycloalkanes, olefins, alkylaromatics, etc.). The dehydrogenated product depends in part on the feedstock selected. For example, alkanes may be dehydrogenated to form olefins, diolefins, alkynes, etc., and olefins may be dehydrogenated to form diolefins, alkynes, etc. One preferred class of feedstock comprises $C_2-C_4$ alkanes. One preferred process embodiment comprises the oxidative dehydrogenation of $C_2-C_5$ alkanes to form the corresponding mono-olefins. In general, the process is conducted within the parameters of the oxidative dehydrogenation art, but uses a novel catalyst.

The rate of molten salt mixture withdrawal from the methane contact zone is desirably balanced with the rate of molten salt mixture passing from the oxygen contact zone to the methane contact zone so as to maintain a substantially constant inventory of molten salt mixture in the methane contact zone, thereby enabling steady-state operation of synthesizing system.

The present invention is further illustrated by reference to the following Examples.

EXAMPLES

In the Examples, methane contact runs were made at about atmospheric pressure in a concentric alumina tube reactor (1-inch inside diameter, 14 inches in length). The gases were sparged via a ½-inch OD alumina tube, fitted with a ¼-inch OD alumina thermowell, into the closed alumina tube reactor. The gases bubbled through the molten salt mixture and travelled along the outside of the sparge tube and were collected overhead. The entire reactor was placed in a 1½-inch ID tube furnace. The calculated L/D ratios were determined by the 1-inch tube diameter and the volume of the molten salt mixture in powdered form at room temperature. Conversions were low due to bubble size constraints and subsequent poor gas/catalyst contact. Larger L/D ratios and/or smaller bubble sizes would have increased the methane conversion. Small bubble sizes could have been achieved by sparging the gases through grates or by placing inerts such as alumina, silicon carbide, and silica particles dispersed in the molten salt mixture.

The reactor material of construction is not limited to alumina; however, the material should be prudently chosen to avoid adverse reaction with the potentially corrosive properties of some of the molten salt mixture. The reactor is brought up to temperature under a flow of heated nitrogen or argon and then switched to methane at the start of the run.

Unless otherwise indicated, all methane contact runs described in the Examples had a duration of two minutes. At the end of each methane contact run, the reactor was flushed with nitrogen or argon and the solids were regenerated under a flow of heated air (usually at 800° C. for 30 minutes). The reactor was then again flushed with nitrogen or argon and the cycle repeated. Unless indicated otherwise, the results reported below are based on the cumulative samples collected after the contact solids were "equilibrated" (i.e., after the aberrant characteristics of the fresh contact solids had dissipated). This allows more meaningful comparison between the contact solids within the scope of the present invention and other contact solids. Three to six cycles of methane contact and regeneration are generally sufficient to equilibrate the contact solids.

EXAMPLE I

A powder mixture of 32.1 weight percent lithium carbonate, 33.4 weight percent sodium carbonate, and 34.5 weight percent potassium carbonate was placed in the reactor tube. A ternary eutectic mixture was formed upon heating to the reaction temperature. The methane was bubbled through the molten salt mixture at 200 ml./min. The results are shown in Table 2.

TABLE 2

| L/D | Temp., °C. | Conv., % | $C_2+$, % |
|---|---|---|---|
| 7 | 848 | 15 | 23 |
| 7 | 875 | 20 | 24 |

EXAMPLE II 50 weight percent of the ternary eutectic mixture of Example I was combined with 50 weight percent of sodium manganese oxide in the reactor tube. A molten salt mixture was formed upon heating to the reaction temperature. The methane was bubbled through the molten salt mixture. The results are shown in Table 3 for the 0–2 minute portion of the run and in Table 4 for the 2–4 minute portion of the run. The melt was homogeneous in nature.

TABLE 3

| Flow Rate, ml. | L/D | Temp., °C. | Conv., % | $C_2+$, % | Coke, % |
|---|---|---|---|---|---|
| (275) | 7 | 851 | 7.1 | 55 | 14.0 |
|  |  | 853 | 6.9 | 64 | 10.0 |
|  |  | 854 | 17.2 | 65 | 11.8 |
|  |  | 854 | 7.2 | 55 | 14.2 |
| (275) | 7 | 870 | 5.5 | 73 | 5.7 |
|  |  | 877 | 97.5 | 0 | 8.2 |
|  |  | 879 | 6.4 | 65 | 11.5 |
| (275) | 7 | 901 | 16.6 | 20 | 7.5 |
|  |  | 904 | 12.1 | 29 | 21.8 |

TABLE 4

| Flow Rate, ml. | L/D | Temp., °C. | Conv., % | $C_2+$, % | Coke, % |
|---|---|---|---|---|---|
| (275) | 7 | 853 | 4.0 | 96 | 10.0 |
|  |  | 854 | 6.1 | 75 | 11.8 |
|  |  | 870 | 4.3 | 93 | 5.7 |
|  |  | 879 | 4.3 | 96 | 11.5 |
|  |  | 901 | 6.2 | 98 | 7.5 |
|  |  | 904 | 6.0 | 49 | 21.8 |

EXAMPLE III

A series of runs were done with 50 weight percent mixture of sodium manganese oxide with sodium tungsten oxide, sodium molybdenum oxide, and sodium sulfur oxide. The methane was bubbled through the molten salt mixture at 200 ml./min. The results are shown in Table 5.

TABLE 5

| Additive | L/D | Temp., °C. | Conv., % | $C_2+$, % |
|---|---|---|---|---|
| $Na_2WO_4$ | 7 | 862 | 2.5 | 96 |
| $Na_2MoO_4$ | 6 | 857 | 3.3 | 42 |
| $Na_2SO_4$ | 7 | 855 | 1.0 | 70 |

Systems with $Li_2WO_4$ and $Bi_2Mo_3O_{12}$ were attempted, but failed because the molten salt mixture system crept and plugged the reactor.

EXAMPLE IV

The powder mixture of Example I was combined with 20 weight percent sodium praseodymium oxide ($NaPr_6O_{11}$) and treated to reaction temperature. The methane was bubbled through the molten salt mixture at 200 ml./min., and the L/D was 6. The results are shown for the 0–2 minute portion of the run in Table 6 and for the 2–4 minute portion of the run in Table 7.

TABLE 6

| Temp., °C. | Conv., % | $C_2+$, % | Coke, % |
|---|---|---|---|
| 850 | 3.3 | 23 | 1.0 |
| 856 | 2.0 | 30 | 0.3 |
| 875 | 1.9 | 47 | 0.5 |
| 875 | 1.8 | 40 | 0.8 |
| 902 | 5.1 | 16 | 0.9 |
| 905 | 3.0 | 41 | 0.8 |

TABLE 7

| Temp., °C. | Conv., % | $C_2+$, % | Coke, % |
|---|---|---|---|
| 850 | 3.3 | 23 | 1.0 |
| 856 | 2.2 | 33 | 0.3 |
| 875 | 2.7 | 39 | 0.5 |
| 875 | 2.4 | 40 | 0.8 |
| 902 | 3.5 | 40 | 0.9 |
| 905 | 10.2 | 37 | 0.8 |

EXAMPLE V

The powder mixture of Example I was combined with 20 weight percent supported contact agent composed of 12.5 weight percent sodium permanganate on magnesia. The metal oxide support/molten salt mixture appear heterogeneous in nature since the metal oxide support remained a separate entity. The methane was bubbled through the molten salt mixture at 200 ml./min. and the L/D was 8. The test results are shown for the 0–2 minute portion of the run in Table 8, and for the 2–4 minute portion of the run in Table 9.

TABLE 8

| Temp., °C. | Conv., % | $C_2+$, % | Coke, % |
|---|---|---|---|
| 850 | 3.3 | 20 | 2 |
| 851 | 2.4 | 26 | 1 |
| 875 | 2.5 | 40 | 1 |
| 875 | 2.4 | 45 | 1 |
| 899 | 3.5 | 51 | 1 |
| 903 | 3.1 | 54 | — |

TABLE 9

| Temp., °C. | Conv., % | $C_2+$, % | Coke, % |
|---|---|---|---|
| 850 | 2.7 | 29 | 2 |
| 851 | 2.9 | 34 | 1 |
| 875 | 2.9 | 46 | 1 |
| 875 | 2.7 | 54 | 1 |
| 899 | 3.0 | 58 | 1 |
| 903 | 3.2 | 57 | — |

EXAMPLE VI

A powder mixture composed of 32.1 weight percent lithium carbonate, 33.4 weight percent sodium carbonate, and 34.5 weight percent potassium carbonate was combined with the indicated weight percent of manganese oxide in the reactor tube. A molten salt mixture was formed upon heating to the reaction temperature. The methane was bubbled through the molten salt mixture at 200 ml./min. The results are shown for the 0–2 minute portion of the run in Table 10, and for the 2–4 minute portion of the run in Table 11.

TABLE 10

| $NaMnO_4$, % | L/D | Temp., °C. | Conv., % | $C_2+$, % | Coke, % |
|---|---|---|---|---|---|
| 10 | 2.2 | 825 | 0.7 | 39 | — |

TABLE 10-continued

| NaMnO4, % | L/D | Temp., °C. | Conv., % | C2+, % | Coke, % |
|---|---|---|---|---|---|
|  |  | 850 | 1.2 | 56 | — |
|  |  | 900 | 2.8 | 56 | — |
|  | 4.3 | 825 | 0.9 | 46 | — |
|  |  | 850 | 0.9 | 40 | — |
|  |  | 900 | 2.5 | 53 | — |
| 50 | 7.0 | 851 | 7.2 | 55 | 14.2 |
|  |  | 853 | 6.9 | 64 | 10.0 |
|  |  | 854 | 17.2 | 65 | 11.8 |
|  |  | 870 | 5.5 | 73 | 5.7 |
|  |  | 879 | 6.4 | 65 | 11.5 |
|  |  | 901 | 16.6 | 20 | 7.5 |
|  |  | 909 | 12.1 | 29 | 21.8 |

TABLE 11

| NaMnO4, % | L/D | Temp., °C. | Conv., % | C2+, % | Coke, % |
|---|---|---|---|---|---|
| 10 | 2.2 | 827 | 1.0 | 54 | — |
|  |  | 850 | 1.0 | 62 | — |
|  |  | 900 | 3.6 | 46 | — |
|  | 4.3 | 825 | 0.8 | 72 | — |
|  |  | 850 | 1.0 | 38 | — |
|  |  | 900 | 3.3 | 55 | — |
| 50 | 7.0 | 851 | 4.3 | 82 | 14.2 |
|  |  | 853 | 4.0 | 96 | 10.0 |
|  |  | 854 | 6.1 | 75 | 11.8 |
|  |  | 870 | 4.3 | 93 | 5.7 |
|  |  | 879 | 4.3 | 96 | 11.5 |
|  |  | 901 | 6.2 | 48 | 7.5 |
|  |  | 909 | 6.0 | 49 | 21.8 |

EXAMPLE VII

Example V was repeated, except that 10 percent of the supported contact agent composed of 12.5 weight percent NaMnO2 on magnesia was combined with the molten salt mixture of Example VI. The results are shown for the 0-2 minute portion of the run in Table 17, and for the 2-4 minute portion of the run in Table 13.

TABLE 12

| L/D | Temp., °C. | Conv., % | C2+, % | Coke, % |
|---|---|---|---|---|
| 4.3 | 848 | 2.1 | 20 | 0.2 |
|  | 850 | 1.8 | 32 | — |
|  | 854 | 2.0 | 23 | 0.2 |
|  | 855 | 1.8 | 27 | 0.2 |

TABLE 13

| L/D | Temp., °C. | Conv., % | C2+, % | Coke, % |
|---|---|---|---|---|
| 4.3 | 848 | 1.8 | 28 | 0.2 |
|  | 850 | 2.0 | 30 | — |
|  | 854 | 2.0 | 31 | 0.2 |
|  | 855 | 1.9 | 33 | 0.2 |

EXAMPLE VIII

Example VII was repeated, except that 10 percent NaMnO2/MgO was replaced by 10 percent NaMnO4. The results for the 0-2 and 2-4 minute portions of the runs are shown in Tables 14 and 15, respectively.

TABLE 14

| L/D | Temp., °C. | Conv., % | C2+, % |
|---|---|---|---|
| 2 | 827 | 0.7 | 39 |
| 2 | 850 | 1.2 | 56 |

TABLE 14-continued

| L/D | Temp., °C. | Conv., % | C2+, % |
|---|---|---|---|
| 2 | 900 | 2.8 | 56 |
| 4 | 825 | 0.9 | 46 |
| 4 | 850 | 0.8 | 40 |
| 4 | 900 | 2.5 | 53 |

TABLE 15

| L/D | Temp., °C. | Conv., % | C2+, % |
|---|---|---|---|
| 2 | 827 | 1.0 | 54 |
| 2 | 850 | 1.0 | 62 |
| 2 | 900 | 3.6 | 46 |
| 4 | 825 | 0.8 | 72 |
| 4 | 850 | 1.0 | 38 |
| 4 | 900 | 3.3 | 55 |

EXAMPLE IX

A powder of cerium fluoride was combined with 9.1 weight percent of sodium manganese oxide in the reactor tube. A molten salt mixture was formed upon heating to the reaction temperature. The results are shown for a methane bubble rate of 200 ml./min. in Table 16.

TABLE 16

| Temp., °C. | Run Portion, min. | Conv., % | C2+, % | Coke, % |
|---|---|---|---|---|
| 850 | 0-1 | 1.9 | 93 | 2.6 |
| 875 | 0-2 | 1.9 | 81 | 0.5 |
| 900 | 0-2 | 2.1 | 71 | 0.1 |

EXAMPLE X

A powder mixture of sodium carbonate was combined with 6.4 weight percent of metal oxide in the reactor tube. A molten salt mixture was formed upon heating to the reaction temperature. The results are shown for a methane bubble rate of 200 ml./min. in Table 17.

TABLE 17

| Temp., °C. | Conv., % | C2+, % |
|---|---|---|
| 855 | 1.7 | 64 |
| 875 | 2.3 | 69 |

What is claimed is:

1. A method for conversion of methane to higher hydrocarbons which comprises contacting a hydrocarbon gas comprising methane with a mixture comprising molten salt and at least one reducible metal oxide contact agent at a selected temperature within the range of about 500° to about 1000° C. to produce higher hydrocarbons and water.

2. The method of claim 1 wherein said mixture comprises additionally a support comprising at least one member of a group consisting of oxides of silicon, oxides of alkaline earth metals, and mixed oxides of silicon and at least one alkaline earth metal.

3. The method of claim 1 wherein said contact agent is selected from a group consisting of oxides of maganese, tin, indium, germanium, antimony, lead, bismuth, and mixtures thereof.

4. The method of claim 1 comprising additionally at least one alkali metal.

5. The method of claim 2 wherein said support comprises at least two oxides.

6. The method of claim 5 wherein said support comprises magnesia and silica.

7. The method of claim 2 wherein said support comprises magnesia.

8. The method of claim 2 wherein said support comprises silicon oxide.

9. The method of claim 3 wherein said contact agent comprises manganese oxide.

10. The method of claim 9 wherein the contact agent additionally comprises an alkali metal.

11. The method of claim 1 wherein said molten salt comprises an alkali or alkaline earth metal salt selected from a group consisting of halides, phosphates, borates, carbonates, sulfates, tungsten oxides, silicates, molybdenum oxides, and mixtures thereof.

12. The method of claim 10 wherein said metal oxide is dissolved in said molten salt.

13. The method of claim 1 wherein said mixture contains an inert gas dispersing agent.

* * * * *